United States Patent [19]

Matsumoto et al.

[11] Patent Number: 5,776,899
[45] Date of Patent: Jul. 7, 1998

[54] POLYPEPTIDE AND ANTI-HIV AGENT PREPARED THEREFROM

[75] Inventors: Akiyoshi Matsumoto, Hino; Michinori Waki, Higashimurayama, both of Japan

[73] Assignee: Seikagaku Corporation, Tokyo, Japan

[21] Appl. No.: 454,235

[22] PCT Filed: Oct. 12, 1994

[86] PCT No.: PCT/JP94/01706

§ 371 Date: Jun. 13, 1995

§ 102(e) Date: Jun. 13, 1995

[87] PCT Pub. No.: WO95/10534

PCT Pub. Date: Apr. 20, 1995

[30] Foreign Application Priority Data

Oct. 14, 1993 [JP] Japan ............................. 5-280346

[51] Int. Cl.$^6$ .......................... A61K 38/00; A61K 38/04; C07K 5/00; C07K 7/00
[52] U.S. Cl. ................................. 514/14; 530/327
[58] Field of Search ................................. 514/14

[56] References Cited

U.S. PATENT DOCUMENTS

| | | | |
|---|---|---|---|
| 5,068,314 | 11/1991 | Nakamura et al. | 530/317 |
| 5,449,752 | 9/1995 | Fujii et al. | 530/326 |
| 5,571,892 | 11/1996 | Fujii et al. | 530/326 |

FOREIGN PATENT DOCUMENTS

| | | | |
|---|---|---|---|
| 0502198 | 9/1992 | European Pat. Off. | C07K 7/08 |
| 0513613 | 11/1992 | European Pat. Off. | C07K 7/08 |
| 2-500194 | 1/1990 | Japan . | |
| 2-53799 | 2/1990 | Japan . | |
| 2-152987 | 6/1990 | Japan . | |
| 2-167230 | 6/1990 | Japan . | |
| 5-163298 | 6/1993 | Japan . | |
| WO 9204374 | 3/1992 | WIPO . | |

OTHER PUBLICATIONS

Akaji, 1989, "Studies on Peptides. CLXVIII. Synthesis of Three Peptides Isolated from Horseshoe Crab Hemocytes, Tachyplesin I, Tachyplesin II, and Polyphemusin I", *Chem. Pharm. Bull.* 37: 2661–2664.

Kawano et al., 1990, "Antimicrobial Peptide, Tachyplesin I, Isolated from Hemocytes of the Horeshoe Crab", *The Journal of Biological Chemistry* 265: 15365–15367.

Legendre and Szoka, 1993, "Cyclic amphipathic peptide–DNA complexes mediate high–efficiency transfection of adherent mammalian cells", *Proc. Natl. Acad. Sci. USA* 90: 893–897.

Masuda et al., 1992, "Structure–Activity Relationships of tachyplesin analogs as anti–HIV agent" *J. Pharmacobio-Dyn.* 15: s–90.

Masuda et al., 1992, "A Novel Anti–HIV Synthetic Peptide, T–22 ([Tyr$^{5,12}$,Lys$^7$]–Polyphemusin II)", *Biochemical and Biophysical Research Communications* 189: 845–850.

Matsuzaki et al., 1991, "Interactions of an antimicrobial peptide, tachyplesin I, with lipid membranes" *Biochimica and Biophysica Acta* 1070: 259–264.

Miyata et al., 1989, "Antimicrobial Peptides, Isolated from Horseshoe Crab Hemocytes, Tachyplesin II and Polyphemusins I and II:Chemical Structures and Biological Activity", *J. Biochem.* 106: 663–668.

Morimoto, 1991, "Inhibitory Effect of Tachyplesin I on the Proliferation of Human Immunodeficiency Virus in vitro", *Chemotherapy* 37: 206–211.

Murakami et al., 1991, "Direct Inactivation of Tachyplesin I and Its Isopeptides from Horseshoe Crab Hemocytes", *Chemotherapy* 37: 327–334.

Muta et al., 1990, Tachplesins Isolated from Hemocytes of Southeast Asian Horseshoe Crabs (*Carcinoscorpius rotundicauda* and *Tachypleus gigas*): Identification of a New Tachyplesin Tachyplesin, III, and a Processing Intermediate as its Precursor, *J. Biochem.* 108: 261–266.

Nakamura et al., 1988, Tachyplesin, a Class of Antimicrobial Peptide from the Hemocytes of the Horseshoe Crab (Tachpleus tridentatus), *The Journal of Biological Chemistry* 263: 16709–16713.

Nakashimura et al., 1992, "Anti–Human Immunodeficiency Virus Activity of a Novel Synthetic Peptide, T22 ([Tyr–5, 12,Lys–7]Polyphemusin): a Possible Inhibitor of Virus–Cell Fusion", *Antimicrobial Agents and Chemotherapy*, Jun. 1992: 1249–1255.

Shieh et al., 1989, "Synthesis and properties of tachyplesin I, a lipopolysaccharide–binding peptide, from *Tachypleus tridentatus*", *Febs Letters* 252: 121–124.

Shigenaga et al., 1990, "Antimicrobial Tachyplesin Peptide Precursor", *The Journal of Biological Chemistry* 265: 21350–21354.

Tamamura, 1993, "A Comparative study of the solution structures of tachyplesin I and a novel anti–HIV synthetic peptide, T22(Tyr$^{5,12}$, Lys$^7$–polylphemusin II), determined by nuclear magnetic resonance", *Biochimica and Biophysica Acta* 1163: 209–216.

Tokunaga and Iwanaga, 1989, "LPS–binding proteins and peptides", *Taisha (Metabolism)* 26: 429–439.

Yonezawa et al, 1992, "Binding of Tachyplesin I to DNA Revealed by Footprinting Analysis: Significant Contribution of Secondary Structure to DNA Binding and Implication for Biological Action", *Biochemistry* 31: 2998–3004.

*Primary Examiner*—Cecilia J. Tsang
*Assistant Examiner*—Jennifer Harle
*Attorney, Agent, or Firm*—Pennie & Edmonds, LLP

[57] ABSTRACT

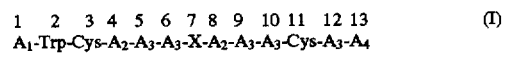
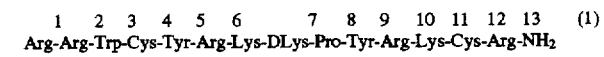

A polypeptide represented by formula (I), and one example of such polypeptide be represented as formula 1 is presented. The above presented polypeptide may be useful in a pharmaceutical composition as an antimicrobial or antiviral agent, specifically as an anti–HIV agent and as a component of the DNA-transfecting systems for gene therapy.

7 Claims, 2 Drawing Sheets

FIG. 1

|  | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Tachyplesin I | Lys | Trp | Cys | Phe | Arg | Val | Cys | Tyr | Arg | Gly | Ile | Cys | Tyr | Arg | Arg | Cys | Arg - NH2 |
| Tachyplesin II | Arg | Trp | Cys | Phe | Arg | Val | Cys | Tyr | Arg | Gly | Ile | Cys | Tyr | Arg | Lys | Cys | Arg - NH2 |
| Tachyplesin III | Lys | Trp | Cys | Phe | Arg | Val | Cys | Tyr | Arg | Gly | Ile | Cys | Tyr | Arg | Lys | Cys | Arg - NH2 |
| Polyphemusin I | Arg | Arg | Trp | Cys | Phe | Arg | Val | Cys | Tyr | Arg | Gly | Phe | Cys | Tyr | Arg | Lys | Cys | Arg - NH2 |
| Polyphemusin II | Arg | Arg | Trp | Cys | Phe | Arg | Val | Cys | Tyr | Lys | Gly | Phe | Cys | Tyr | Arg | Lys | Cys | Arg - NH2 |

FIG. 2

POLYPEPTIDE AND ANTI-HIV AGENT PREPARED THEREFROM

1. FIELD OF THE INVENTION

This invention relates to a novel polypeptide(s) or a pharmaceutically acceptable salt thereof exhibiting a strong affinity to lipopolysaccharides, particularly endotoxins. The polypeptide may be used in a pharmaceutical composition as an anti-viral agent (e.g. anti-HIV agent).

2. BACKGROUND OF THE INVENTION

Two families of antimicrobial polypeptides have been isolated from horseshoe crabs which exhibit an affinity to endotoxins (see, for example. Shigenaga et al., 1990, J. Biol. Chem. 265:21350–21354; Kawano et al., 1990, J. Biol. Chem. 265:15365–15367; Muta et al., 1990, J. Biochem. 108:261–266; Japanese Laid-Open Patent Publication No. 167230/1990; Japanese Laid-Open Patent Publication No. 152987/1990; Japanese Laid-Open Patent Publication No. 53799/1990; Published Searched Application 500194/1990; Miyata et al., 1989, J. Biochem. 106:663–668; Akaji et al., 1989, Chem. Pharm. Bull. 37:2661–2664; Tokunaga and Iwanaga, 1989, Taisha(Metabolism) 26:429–439 ; Shieh et al., 1989, FEBS Lett. 252:121–124; and Nakamura et al., 1988, J. Biol. Chem. 263:16709–16713).

One family, the tachyplesin family has been isolated from the Japanese horseshoe crab Tachypleus. Three tachyplesins, I, II, and III have been identified. A second family, the polyphemusin family has been isolated from the American horseshoe crab, Limulus polyphemus. Two polyphemusins, I and II have been identified; their amino acid sequences are shown in FIG. 1.

Figure 1:
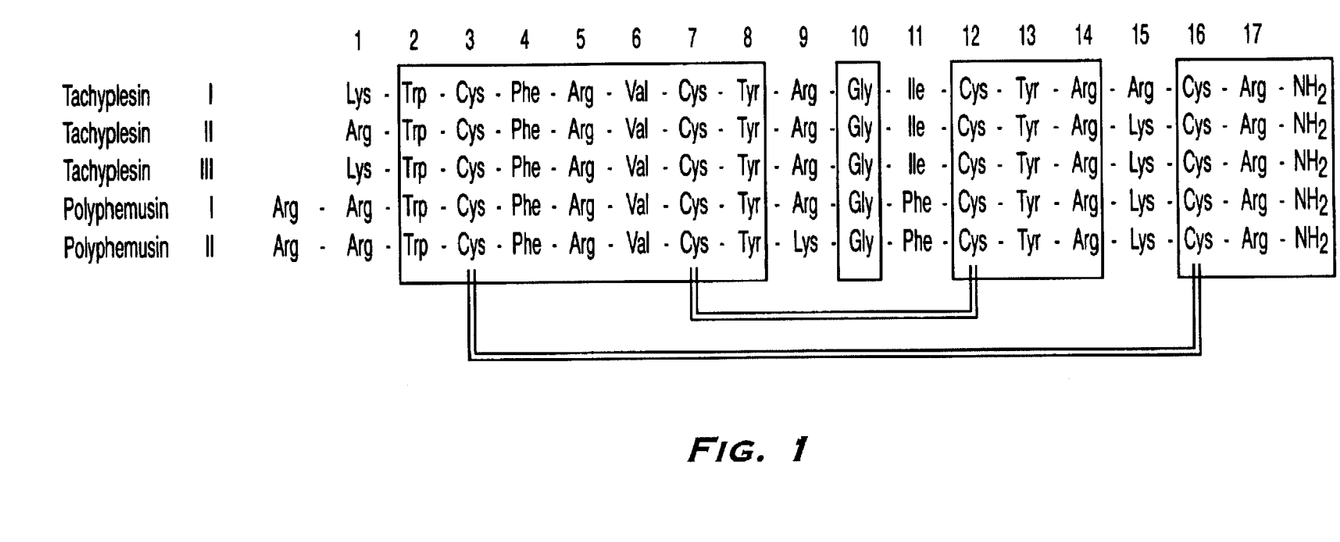
FIG. 1 shows the amino acid sequences of Tachyplesin I, Tachyplesin II, Tachyplesin III, Polyphemusin I, and Polyphemusin II. Conserved amino acids are boxed. The disulfide linkages between Cys-3 or -4 and Cys-16 or -17 and Cys-7 or -8 and Cys-12 or -13 are shown by solid lines.
Figure 2:
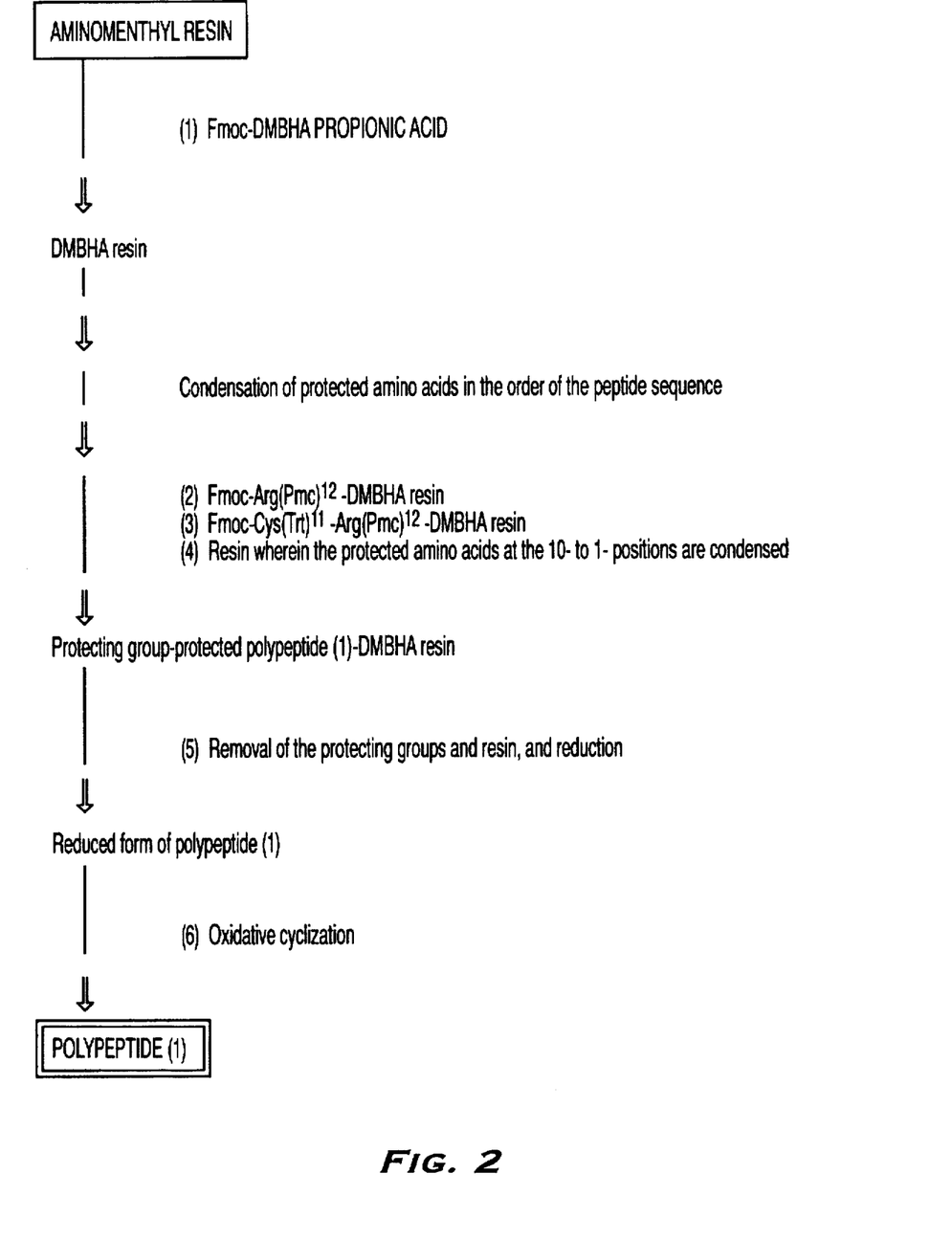
FIG. 2 shows a synthetic scheme for synthesizing polypeptide (1) of the invention.

The polypeptides in both families consist of 17 or 18 amino acid residues and have four conserved regions in common and two disulfide bridges (see FIG. 1).

Both tachyplesins and polyphemusins have been found to inhibit the growth of both Gram-negative and -positive bacteria at low concentrations as well as fungi, such as Candida albicans and form complexes with bacterial lipopolysaccharides (Shigenaga et al., 1990, J. Biol. Chem. 265:21350–21354 and Muta et al., 1990, J. Biochem. 108:261–266). Also, the polypeptides in a tachyplesin family have been found to exhibit some inhibition activity for virus, such as Influenza virus, vesicular stomatitis virus (Murakami et al., 1991, Chemotherapy, 37, 327–334) or human immunodeficiency virus (Morimoto, et al., 1991, Chemotherapy, 37, 206–211). It is very interesting that such a polypeptide with above properties may be one of the key substances which enables the horseshoe crab to adapt with changes in their external environment and to preserve their species from ancient times to now as a living fossil.

On the other hand, with respect to the survival of the highly evolved human beings, development of such drugs is extremely longing that have a prophylactic or therapeutic effect on acquired immune deficiency syndrome (AIDS) caused by infection with human immunodeficiency virus (HIV).

Present inventors and coresearchers have been studied a correlation between molecular structure and anti-HIV activity on the polypeptides with changing or modifying the amino acid of components, taking notice of these polypeptides which are related to the long preservation of the horseshoe crabs. As a result, the past new polypeptides had been invented by us, fundamentally different from the common structure of such the known polypeptides of the horseshoe crabs.

Surprisingly, it was found that these past new polypeptides have an excellent bioactivity whose anti-HIV values are at least 5 times or more higher than that of a known polypeptides of the horseshoe crabs.

Following references had be seen. Nakashima et al., 1992, Antimicrob. Agents Chemother., 36, 1249–1255 ; Masuda et al., 1992, Biochem. Biophys. Res. Commun., 189, 845–850 ; Tamamura et al., 1993, Chem. Pharm. Bull., 41, 978–980 ; Tamamura et al., 1993, Biochim. Biophys. Acta, 1163, 209–216 ; Masuda et al., 1992, J. Pharmacobio. Dyn., 15, s-90 ; International Laid-Open Publication WO 92/04374 ; Japanese Laid-Open Patent Publication No.163298/1993.

(Hereinafter, among the new polypeptides, the compound T-22 is referred to the best mode compound of the representatives.) Having examined the structural requirements for exhibiting the activity of the new polypeptide consisting of 16 to 18 amino acids as represented by the T-22 compound, the inventors and coresearchers arrived at some inventive concepts of a minimum essential structure.

In general, when an exogenous peptide of relatively high molecular weight is administered into human body, it is often recognized as an alien substance by the self defence function of the human body. As a result, it is likely to become an antigenic substance. When used for a medical purpose, it is desirable that a peptide-based bioactive substance may be a compound of low molecular weight in order to reduce its likelihood of being recognized as an alien substance. It is also required that the substance may have a high potency.

The T-22 compound was found to be a polypeptide consisting of 18 amino acid residues. The objective of our investigation was to maintain the same level of anti-HIV potency as that of the T-22 compound, while reducing the number of amino acid residues. As a result, we succeeded in reducing the number of residues by 4 (four). As long as the compound has the basic structure, its activity does not decline even when a specific region is modified. Moreover, by the said modification, we discovered the novel polypeptide having such essential structure that can provide a broader range of physicochemical characteristics, and also a broader selection in therapeutic methods, i.e. increasing/decreasing of the hydrophilicity and lipophilicity (affinity to lipid); selective accumulation in a specific organ and/or cell; and increasing/decreasing its residence time within the human body; and possible development of formulations.

3. SUMMARY OF THE INVENTION

The present invention relates to a novel polypeptide(s) which is derived from the past new polypeptides with a high anti-HIV activity invented based on the known high endotoxin affinity polypeptides of horseshoe crabs, but has a significant difference.

The past new polypeptides consist of 16–18 amino acid residues, 4 cysteine or 2 systine residues and antiparallel β sheet structure with β turn as a turning position. Like the past new polypeptides, the polypeptides of the present invention have an antiparallel β sheet structure with possibly β turn located in the X at 7th position. However, in the polypeptides of the present invention, the numbers of amino acid residues and cystein residues are reduced by four and two, respectively. Moreover, biological activity does not decrease even when a specific region is modified. The polypeptides of the present invention may be used as an anti-HIV reagent and as a component of the DNA-transfecting systems for gene therapy. As will be detailed in the Section 6, infra, the polypeptides of the invention have anti-HIV values that are significantly higher than the past new polypeptides derived from the known high endotoxin affinity polypeptides of horseshoe crabs.

3.1 DEFINITIONS

Peptide sequences defined herein are represented by three letter abbreviations for amino acid residues and substituted amino acid residues as follows:

Ala (alanine); Arg (arginine); Cys (cysteine); Ile (isoleucine); Gly (glycine); Leu (leucine); Lys (lysine); Orn (ornithine); Phe (phenylalanine); Pro (proline); Trp (tryptophan); Tyr (tyrosine); Val (valine); DArg (D-arginine); DLys (D-lysine); DOrn (D-ornithine); Ac-Arg (N-α-acetyl arginine); FTC-Arg (N-α-fluororescein thiocarbamoyl arginine); Laur-Arg (N-α-lauroyl arginine); Myr-Arg (N-α-myristoyl arginine); Nicot-Arg (N-α-nicotinoyl arginine); Oct-Arg (N-α-octanoyl arginine); Parm-Arg ((N-α-palmitoyl arginine); Parm-Orn (N-α-palmitoyl ornithine); PTC-Arg (N-α-phenyl thiocarbamoyl arginine); ε-N-Ac-DLys (ε-N-α(ε-N-ωaminoacetyl-D-lysine) and ε-N-But-DLys (ε-N-ω-aminobutyryl-D-lysine).

The following terms, as used herein, will have the meanings indicated:

HIV=human immunodeficiency virus (all variants)
MOI=multiplicity of infection
SI=selectivity index (ratio of $CC_{50}$ to $EC_{50}$)

5. DETAILED DESCRIPTION OF THE INVENTION

The present invention is accomplished based on the above aspects, and is related to a novel polypeptide represented by the following formula $$A_1\text{-Trp-Cys-}A_2\text{-}A_3\text{-}A_3\text{-X-}A_2\text{-}A_3\text{-}A_3\text{-Cys-}A_3\text{-}A_4 \quad (I)$$

or salt thereof in which $A_1$ is a basic amino acid residue, or a peptide residue having one or at least two basic amino acids, selected from the group consisting of lysine, arginine and ornithine, said basic amino acid residue or peptide residue in which N-α hydrogen atom of amino terminal end of said amino acid residue may be replaced with an acyl group or a substituted thiocarbamoyl group, forming N-α acyl substituted basic amino acid residue, N-α acyl substituted peptide residue, N-α substituted thiocarbamoyl group substituted basic amino acid residue or N-α substituted thiocarbamoyl group substituted peptide residue;

$A_2$ is a tyrosine or phenylalanine residue;

$A_3$ is a lysine or arginine residue;

$A_4$ is an —OH (derived from a carboxyl group) or an —$NH_2$ (derived from an acid amide group);

X is a peptide residue selected from the group consisting of the peptides represented by D-ornithyl-proline, prolyl-D-ornithine, D-lysyl-proline, prolyl-D-lysine, D-arginyl-proline, prolyl-D-arginine, glycyl-ornithine, ornithyl-glycine, glycyl-lysine, lysyl-glycine, glycyl-arginine and arginyl-glycine, in which the hydrogen atom of the ω-amino group of D-lysine, L-lysine, D-ornithine and L-ornithine may be replaced by an ω-amino acyl group, and said peptide residue is connected to the amino acid residues at the 6th and the 8th positions via peptide bond per se;

Trp is a tryptophan residue; and

Cys is a cysteine residue; and the cysteine residues at the 3- and 11- positions may be linked through a disulfide linkage.

Specific examples of the polypeptides of the invention represented by the formula (I), are shown in Table 1 and are numbered (1) to (25).

Each symbol denotes the corresponding amino acid residue by the internationally admitted three-letter expression (see Section 3.0., supra).

TABLE 1

| | 1 | 2 | 3 | 4 | 5 | 6 | 7 | 8 | 9 | 10 | 11 | 12 | 13 |
|---|---|---|---|---|---|---|---|---|---|---|---|---|---|
| (I) | $A_1$ | —Trp— | Cys— | $A_2$ | —$A_3$ | —$A_3$ — | X | — $A_2$ | —$A_3$ | —$A_3$ | —Cys— | $A_3$ — | $A_4$ |
| (1) | Arg— | Arg —Trp | —Cys— | Tyr— | Arg— | Lys — | DLys—Pro — | Tyr— | Arg— | Lys— | Cys— | Arg— | $NH_2$ |
| (2) | | Arg — | Trp—Cys— | Tyr— | Arg— | Lys — | DLys—Pro — | Tyr— | Arg— | Lys— | Cys— | Arg— | $NH_2$ |
| (3) | Arg—Arg | —Trp—Cys— | | Tyr— | Arg— | Lys — | Lys—Gly — | Tyr— | Arg— | Lys— | Cys— | Arg— | $NH_2$ |
| (4) | | Arg — | Trp—Cys— | Tyr— | Arg— | Lys — | Lys—Gly — | Tyr— | Arg— | Lys— | Cys— | Arg— | $NH_2$ |
| (5) | Arg—Arg | —Trp—Cys— | | Tyr— | Arg— | Lys — | Pro—DLys — | Tyr— | Arg— | Lys— | Cys— | Arg— | $NH_2$ |
| (6) | Arg—Arg | —Trp—Cys— | | Tyr— | Arg— | Lys — | DOrn—Pro — | Tyr— | Arg— | Lys— | Cys— | Arg— | $NH_2$ |
| (7) | Arg—Arg | —Trp—Cys— | | Tyr— | Arg— | Lys — | Pro—DArg — | Tyr— | Arg— | Lys— | Cys— | Arg— | $NH_2$ |
| (8) | Arg—Arg | —Trp—Cys— | | Tyr— | Arg— | Lys — | Gly—Lys — | Tyr— | Arg— | Lys— | Cys— | Arg— | $NH_2$ |
| (9) | Arg—Arg | —Trp—Cys— | | Tyr— | Arg— | Lys — | Arg—Gly — | Tyr— | Arg— | Lys— | Cys— | Arg— | $NH_2$ |
| (10) | Arg—Arg | —Trp—Cys— | | Tyr— | Arg— | Lys — | Gly—Arg — | Tyr— | Arg— | Lys— | Cys— | Arg— | $NH_2$ |
| (11) | Lys—Arg | —Trp—Cys— | | Tyr— | Lys— | Arg — | DLys—Pro — | Tyr— | Lys— | Arg— | Cys— | Arg— | $NH_2$ |
| (12) | Lys—Lys | —Trp—Cys— | | Phe— | Arg— | Lys — | DLys—Pro — | Phe— | Arg— | Lys— | Cys— | Arg— | $NH_2$ |
| (13) | Arg—Lys | —Trp—Cys— | | Tyr— | Lys— | Arg — | DLys—Pro — | Tyr— | Arg— | Arg— | Cys— | Lys— | $NH_2$ |

TABLE 1-continued

| | | | | |
|---|---|---|---|---|
| (14) | Ac— | Arg—Arg—Trp—Cys—Tyr—Arg—Lys— | DLys—Pro— | Tyr—Arg—Lys—Cys—Arg—NH₂ |
| (15) | Oct— | Arg—Arg—Trp—Cys—Tyr—Arg—Lys— | DLys—Pro— | Tyr—Arg—Lys—Cys—Arg—NH₂ |
| (16) | Laur— | Arg—Arg—Trp—Cys—Tyr—Arg—Lys— | DLys—Pro— | Tyr—Arg—Lys—Cys—Arg—NH₂ |
| (17) | Myr— | Arg—Arg—Trp—Cys—Tyr—Arg—Lys— | DLys—Pro— | Tyr—Arg—Lys—Cys—Arg—NH₂ |
| (18) | Parm— | Arg—Arg—Trp—Cys—Tyr—Arg—Lys— | DLys—Pro— | Tyr—Arg—Lys—Cys—Arg—NH₂ |
| (19) | FTC— | Arg—Arg—Trp—Cys—Tyr—Arg—Lys— | DLys—Pro— | Tyr—Arg—Lys—Cys—Arg—NH₂ |
| (20) | PTC— | Arg—Arg—Trp—Cys—Tyr—Arg—Lys— | DLys—Pro— | Tyr—Arg—Lys—Cys—Arg—NH₂ |
| (21) | Nicot— | Arg—Arg—Trp—Cys—Tyr—Arg—Lys— | DLys—Pro— | Tyr—Arg—Lys—Cys—Arg—NH₂ |

(22)  Arg—Arg—Trp—Cys—Tyr—Arg—Lys(ε-N—Ac)—DLys—Pro—Tyr—Arg—Lys—Cys—Arg—NH₂

(23)  Arg—Arg—Trp—Cys—Tyr—Arg—Lys(ε-N—But)—DLys—Pro—Tyr—Arg—Lys—Cys—Arg—NH₂

(24)  Parm—Arg—Arg—Trp—Cys—Tyr—Arg—Lys(ε-N—But)—DLys—Pro—Tyr—Arg—Lys—Cys—Arg—NH₂

(25)  Parm—Orn—Arg—Trp—Cys—Tyr—Arg—Lys(ε-N—But)—DLys—Pro—Tyr—Arg—Lys—Cys—Arg—NH₂

The above-mentioned polypeptide with a high anti-HIV activity consists of 16-18 amino acid residues. The above-mentioned polypeptide with a high anti-HIV activity consists of 16–18 amino acid residues. In the best mode compound (hereinafter abbreviated as "n-18 polypeptide" or T-22), it is considered that structural factors for exhibiting high activity are essential of existence of 4(four) cysteine residues, of four or five aromatic amino acid residues, of eight basic amino acid residues and of one glycine residue. Moreover, with respect to the positional relationship of the n-18 polypeptide as show following formula (A), the properties of the amino acid residues at 2- to 17- positions are tightly fixed. And at the first position of the n-18 polypeptide, a structure-activity correlation was found in which the relative values of anti-HIV activity expressed increases with the increase of the number of the amino acid residue.

The n-18 polypeptide is denoted as the following formula (A)

in which $A_1$ is no more than two amino acids selected from the group consisting of lysine and arginine;

$A_2$ is a tyrosine, phenylalanine or tryptophan residue;

$A_3$ is an arginine or lysine residue;

$A_4$ is at least one and no more than two amino acids selected from the group consisting of lysine and arginine;

$A_5$ is an —OH (derived from the carboxylic group); or an —NH₂ (derived from the amide group);

Cys is a cysteine residue; and

Gly is a glycine residue.

In a specific embodiment, the cysteine residues at the 3- and 16- positions and/or the cysteine residues at the 7- and 12- positions may be linked through a disulfide linkage (—S—S—).

In the n-18 polypeptide, the turning position with possibly beta-turn structure is located at the 9- and 10-positions. And the peptide part of the 3-position to the 8-position and the peptide part of the 11-position to the 16-position face each other.

Like the n-18 polypeptide, the polypeptides of the present invention have an antiparallel β sheet structure due to the existence of intramolecular hydrogen bonding and disulfide linkage (—S—S—) with cysteine residues. While in the polypeptides of the present invention, the turning position with possibly β turn structure is so located in the X at 7th position that the peptide part of the 3-position to the 6-position and the peptide part of the 8-position to the 11-position face each other.

In the present invention, the relationship of the number of amino acid residues at the 1- position of the formula of the present invention is the same as that for the n-18 polypeptide.

It is confirmed that replacement of the hydrogen atom of an α-amino group of the N terminal amino acid residue at the said position by an acyl group or a substituted thiocarbamoyl group is important to exhibit high anti-HIV activity of the novel polypeptide represented by the denoted formula. By selecting different properties of the acyl or the substituted thiocarbamoyl group, it has become possible to give the novel polypeptide of the invention hydrophilicity, affinity for lipids, distinct fluorescence properties, and etc. For example, the fluorescence properties of the fluorescein substituted thiocarbamoyl group in the polypeptides of this invention can be used as a highly sensitive reporter dye for various purposes. See, for example, Brand and Witholt in "Methods in Enzymology," Vol. 11, page 776–856, ed. by Hirs, Academic Press, New York, N.Y.(1967); Brand and Gohlke, 1972, Annu. Rev. Biochem. 41:843–868; Stryer, 1978, Annu. Rev. Biochem. 47:819–846.

Moreover, it is very important and useful that the fluorescein substituted thiocarbamoylated polypeptides of this invention could exhibit even higher anti-HIV activity. Thus, the said polypeptides of this invention with fluorescence properties can be used as an important tool for elucidating the manifestation-mechanism of anti-HIV activity of the polypeptides of this invention. For example, fate, metabolism or distribution within body, organ, tissue or cell infected or non-infected with HIV after administration can be detected by fluorescence microscopy. In molecular level, information on the subtle conformational changes of the said polypeptides interacting with receptor molecule within the cells can be obtained by the use of the intrinsic fluorescence probes of the said polypeptides. Isolation and identification of the receptor molecule itself may be possible by the use of the fluorescence probes.

Furthermore, via an acyl group or a substituted thiocarbamoyl, it has become possible to give the novel polypeptide bioactivity of compounds such as a sugar chain compounds, a lipid compounds, a nucleic acid compounds, other kinds of peptides or proteins, etc. It plays an important role in the activity manifestation of the novel polypeptide of the invention that the properties of the amino acid residue at the 4th to 6th positions and at the 8th to 10th positions of the formula of the present invention are the same repeated ones. With respect to formation of the three-dimensional structure of the novel polypeptide of this invention, an amino acid sequence order of the peptide is important that easily makes peptide structural parts represented at 3rd to 7th positions and 7th to 11th positions in the same planar structure in opposite manner and the peptide residue consisting of two amino acids represented X at 7th position as a turning point. In case the cysteines at position 3- and 7- are linked through a disulfide linkage, the following three-dimensional structure formed by the peptide backbone of the novel polypeptide of this invention is important characteristics of the invention. That is to say; turn structure of the peptide residue X at 7th position, which consists of a pair of glycine and basic amino acid or of proline and D-form of basic amino acid (in principle, hydroxyproline may be substituted with proline having the same effect) is necessary factor to form the same planar structure with β- sheet structure. The disulfide side chain linked 3- with 11- positions of cysteine residues and the basic side chains of basic amino acid residues at 5- and 9-positions are on the same side of backbone plane, while the aromatic side chains of aromatic amino acid residues at 4- and 8- positions and the basic side chains of basic amino acid residues at 6- and 10- positions are on the opposite side of backbone plane. Formation of these three-dimensional above mentioned structure is important. Thus the novel polypeptide represented by above denoted formula was invented with such three-dimensional structure, resulting in reduction of 4(four) amino acid residues compared with n-18 polypeptide.

Furthermore, like the n-18 polypeptide(s), the polypeptides of the present invention exhibit very basic characteristics. Due to their basic nature, the polypeptide(s) of the present invention may form a salt by acid addition. For example, the polypeptide forms a salt with an inorganic acid (hydrochloric acid, hydrobromic acid, phosphoric acid, nitric acid, sulfuric acid or the like) or an organic carboxylic acid (acetic acid, halo acetic acid such as trifluoroacetic acid, propionic acid, maleic acid, succinic acid, malic acid, citric acid, tartaric acid, salicylic acid and an acidic sugar (glucuronic acid, galacturonic acid, gluconic acid, ascorbic acid or the like), an acidic polysaccharide (hyaluronic acid, chondroitin sulfate, alginic acid or the like) or an organic sulfonic acid (methanesulfonic acid, p-toluenesulfonic acid or the like) including sulfonic acid sugar ester such as chondroitin sulfates.

The following is a more detailed description of the novel polypeptide of the present invention.

5.1 PREPARATION OF POLYPEPTIDES

The novel polypeptide of the invention can be prepared by methods known in the art, for example, solid-phase synthesis techniques described in "Solid-Phase Peptide Synthesis", Stewart & Young, Pierce Chemical Company, Rockford, Illinois (1984). Namely, a straight-chain polypeptide of the invention having the above formula (I) can be obtained by linking the carboxyl group of an N-protected arginine at the 12-position to an insoluble resin having amino groups directly attached or alternatively attached through a spacer having a functional group capable of linking to a carboxyl group (e.g. one capable of converting the carboxyl group of arginine to a p-carboxymethylbenzylester). The amino group of the insoluble resin having the arginine (Arg) residue at the 12-position after deblocking the N -protecting group is capable of successively linking, according to the solid phase method, with the respective protected amino acids of the 11-position to the 1-position of the amino acid sequence represented by the following formula (I)

$$1\quad 2\quad 3\quad 4\quad 5\quad 6\quad 7\quad 8\quad 9\quad 10\quad 11\quad 12\quad 13 \quad (I)$$
$$A_1-Trp-Cys-A_2-A_3-A_3-X-A_2-A_3-A_3-Cys-A_3-A_4$$

[wherein $A_1$, $A_2$, $A_3$, $A_4$, Cys, Trp and X are as defined in the above formula (I)].

In case that N-α acyl amino acid residue or N-α acyl peptide residue is selected in $A_1$ where the hydrogen atom at the N-α position of the amino terminal amino acid residue is replaced by acyl groups, the N terminal amino group of the said peptide resin is acylated with the corresponding acid anhydride or the corresponding acid by use of condensing agents to the acyl group to afford N-acyl peptide resin. Followed by cleavage of the insoluble resin and protecting groups on the amino acids, the straight-chain polypeptide of the invention having the above formula (I) can be obtained. In case that N-α-substituted thiocarbamoyl amino acid residue or N-α-substituted thiocarbamoyl peptide residue in $A_1$ of the aforementioned formula (I) where the hydrogen atom at the N-α position of the amino terminal amino acid residue is replaced by substituted thiocarbamoyl groups, the N-terminal N-α-substituted thiocarbamoyl polypeptide of the invention can be obtained by reaction with the substituted isothiocyanate compound under slightly alkaline conditions.

In this instance, the carboxyl terminus of the amino acid residue at the 12-position can be either free ($A_4$ corresponds to —OH) or converted to an acid amide ($A_4$ corresponds to —$NH_2$). Further, in the obtained polypeptide, the two cysteines at the 3- and 11- positions can form a disulfide linkage (—S—S—) through the mercapto groups.

These disulfide linkage may be formed, for example, by air oxidation, or by the method of Atherton, E., et al., 1985, J. Chem. Soc., Perkin Trans. 1, 2065.

Unless otherwise indicated, the individual amino acid used in the aforementioned solid phase synthesis method is in the L-form, and the basic amino acid coupled with a proline at the 7th position denoted by X is limited to D-form.

Any insoluble resin having an amino group can be used in synthesizing the novel polypeptide of the invention, as long as it can link through its amino groups to the carboxyl group of the N-protected arginine or lysine at the C-terminus or in some cases to the carboxyl group of the spacer linked thereto and thereafter can be eliminated (removed). Examples of such insoluble resins include but are not limited to aminomethyl resins (aminomethylated styrene-divinylbenzene copolymers), benzhydrylamine resins, methylbenzhydrylamine resins and aminomethylphenoxymethyl resins and derivatives thereof. When a benzhydrylamine resin, methylbenzhydrylamine resin, dimethoxybenzhydryl amine (DMBHA) resin or aminomethylphenoxymethyl resin is used, an amide is directly obtained by cleavage, but an aminomethyl resin is preferred in view of yield.

As the spacer having a functional group capable of linking to a carboxyl group or having a carboxyl group, there can, for example, be one that is capable of converting the carboxyl group of arginine to a p-carboxymethylbenzyl ester, but there is no particular limitation on the spacer.

The protected amino acid is an amino acid whose functional groups may be protected with a protecting group using procedures known in the art, or various protected amino acids may be purchased commercially. Those skilled in the art will recognize that polypeptide synthetic methods require the use of a protecting group to stabilize a labile side chain of an amino acid to prevent the side chain from being chemically altered during the synthesis process.

A protecting group for the a amino group of an amino acid is selected from the group including but not limited to Boc (t-butyloxycarbonyl) or Fmoc (9-fluorenylmethyloxycarbonyl). A protecting group for the guanidino group of arginine (Arg) is selected from the group including but not limited to Tos (tosyl), $NO_2$ (nitro), Mtr (4-methoxy-2,3,6-trimethylbenzene sulfonyl) or Pmc (2,2,5,7,8-pentamethylchroman-6-sulfonyl). A protecting group for the mercapto group of cysteine (Cys) may be selected from the group including but not limited to Bzl (benzyl), MBzl (4-methoxybenzyl), 4-MeBzl (4-methylbenzyl), Acm (acetamidomethyl), Trt (trityl), Npys (3-nitro-2-pyridinesulfenyl), t-Bu(t-butyl) or t-BuS (t-butylthio), and Mbzl, 4-MeBzl, Trt, Acm and Npys are preferred. A protecting group for the hydroxy group of tyrosine (Tyr) is selected from the group including but not limited to Bzl, C12Bzl (2,6-dichlorobenzyl) or t-Bu, and the hydroxy group may not be protected. A protecting group for the ε- amino group of lysine (Lys) is selected from the group including but not limited to Z (benzyloxycarbonyl), ClZ (2-chlorobenzyloxycarbonyl), Boc or Npys. In case that the hydrogen atom of the side chain ε-amino group of D or L lysine consisting the X at 7th position, the said amino group may be protected with aforementioned Z, ClZ, Boc or Npys. It is preferred to select from these protecting groups an appropriate one that is known to be suitable for the synthesis conditions.

The coupling of protected amino acids can be carried out according to condensation methods known in the art, such as, for example, a DCC (dicyclohexylcarbodiimide) method, DIPCDI (diisopropylcarbodiimide) method [Tartar, A. et al., 1979, J. Org. Chem. 44:5000], active-ester method, mixed or symmetrical acid anhydride method, carbonyldiimidazole method, DCC-HOBt (1-hydroxybenzotriazole) method [K önig W. et al., 1970, Chem. Ber., 103:788, 2024, 2034] or diphenylphosphoryl azide method, but preferably using the DCC method, DCC-HOBt method, DIPCDI-HOBt method or symmetrical acid anhydride method. The condensation reaction may be carried out in an organic solvent such as dichloromethane, dimethylformamide, N-methylpyrrolidone (NMP) or a mixed solvent thereof. A deblocking reagent such as trifluoroacetic acid/ dichloromethane, HCl/dioxane, piperidine/ dimethylformamide (DMF) or NMP is used to deblock the protecting group for an a-amino group. The degree of the progress of condensation reaction in each step of synthesis is pursued by the method of E. Kaiser et al., 1970, Anal. Biochem., 34, 595 (the ninhydrin reaction method).

According to the foregoing methods, a protected peptide resin having a desired amino acid sequence can be obtained.

When an aminomethyl resin derivative is used as the insoluble resin, the protected polypeptide can be removed from the resin, for example, by treating the protected peptide resin with ammonia in an appropriate solvent. The resulting protected peptide is then treated with hydrogen fluoride to obtain a polypeptide amide represented by the above formula and freed of all the protecting groups.

When a benzhydrylamine resin, methylbenzhydrylamine resin, aminomethylphenoxymethyl resin or DMBHA resin [Funakoshi, S. et al., 1988, J. Chem. Soc., Chem. Commun., 382] is used as the insoluble resin, the polypeptide may be removed from the resin and the protecting groups can simultaneously be removed from the polypeptide by treating the protected peptide resin with hydrogen fluoride, TFMSA (trifluoromethanesulfonic acid) [Yajima, H. et al.; "The Peptides" vol. 5, page 65 (1983), published by Academic Press, edited by E. Gross;], TMSOTf (trimethylsilyl triflate) [Fujii, N. et al., 1987, J. Chem. Soc., Chem. Commun., 274] or TMSBr (trimethylsilyl bromide) [Fujii, N. et al.1987, Chem. Pharm. Bull., 35, 3880] or the like.

In a preferred embodiment, the resulting polypeptide is reduced with 2-mercaptoethanol, DTT (dithio-threitol) or the like to make sure that the mercapto groups of the cysteines are in reduced form. The mercapto groups may be subsequently oxidized to obtain a cyclic polypeptide.

The oxidation treatment can be carried out by a known method. Usually, such oxidizing agent as air or a ferricyanate (e.g. potassium ferricyanide) is used.

Alternatively, the polypeptide(s) of the invention may be produced using recombinant DNA technology. Accordingly, the nucleotide coding sequences for the polypeptide(s) of the invention may be cloned and expressed using techniques well known in the art. See, for example, Maniatis et al., Molecular Cloning, A Laboratory Manual, Cold Spring Harbor Laboratory, Cold Spring Harbor, N.Y., 1991.

The polypeptides of the invention can be isolated and purified by means known in the art for polypeptides, for example, extraction, recrystallization, various chromatographies (gel filtration, ion exchange, partition, adsorption, reverse-phase), electrophoresis, counter-current distribution, etc., and reverse-phase high performance liquid chromatography is the most effective.

5.2 USES FOR POLYPEPTIDES

The polypeptide(s) of the invention represented by the formula (I) have an ability to bind to endotoxins, an antibacterial activity, and an activity to hemolyze endotoxin-sensitized hemocytes. Additionally, the polypeptide(s) of the invention possess an antiviral activity. In a specific embodiment, the polypeptide(s) of the invention have anti-HIV activity. As will be detailed in Section 6, infra, the polypeptides of the invention exhibit significantly higher anti-HIV activity than known high endotoxin affinity polypeptides (e.g., Tachyplesins I, II or III or Polyphemusins I or II) exhibits.

Recent development of delivery systems capable of efficiently introducing DNA into the target cell has made practical human gene therapy for genetic diseases, cancer, AIDS and etc. [Morgan and Anderson, Annu. Rev. Biochem., 62, 191–217 (1993)].

The DNA-transfection systems include the use of polycations, calcium phosphate, liposome fusion, retroviruses, microinjection, electroporation and protoplast fusion. However, all of these methods suffer from one or more problems related to either cellular toxicity, poor reproducibility, inconvenience, or inefficiency of DNA delivery [Flegner et al., Proc. Natl. Acad. Sci. USA, 84, 7413–7417 (1987)].

Recently, highly efficient DNA-transfection procedure using cationic lipid-DNA complex or cyclic amphipathic peptide-DNA complex [Legendre and Szoka, Jr., Proc. Natl. Acad. Sci. USA, 90, 893–897 (1993)] has been reported. The peptides that can form a transfecting complex with DNA include gramicidin S, tyrocidine, polymyxin B, polylysine and melittin all with cationic nature. Among these, the most effective cationic peptide is gramicidin S which is known as an amphipathic cyclic decapeptide antibiotic with β-sheet conformation and can permeabilize and disrupt cell membranes. Both a positive charge and amphipathic character of gramicidin S are thought to be important for the high transfection. Considering these structural characteristics, the polypeptides of this invention can be an alternative candidate of gramicidin S for DNA complex with high transfecting ability because of their strongly cationic and amphipathic nature with β-sheet conformation.

In fact, tachyplesin I, one of the parent molecule of the polypeptides of this invention, can permeabilize membranes and bind to DNA similarly to gramicidin S [Matsuzaki et al., Biochim. Biophys. Acta, 1070, 259–264 (1991) and Yonezawa et al., Biochemistry, 31, 2998–3004 (1992)]. Moreover, the solution structure of T-22, one of the polypeptides of this invention (1), was confirmed to be very similar to that of tachyplesin I with amphipathic anti-parallel β-sheet structure [Tamamura et al., Biochim. Biophys. Acta, 1163, 209–216 (1993)].

Therefore, the polypeptides of this invention may be used as a component of the DNA-transfecting systems for gene therapy.

The polypeptide(s) of the present invention therefore may be used in a pharmaceutical composition comprising the polypeptide(s) of the invention or salt thereof and a pharmaceutically acceptable carrier selected in accordance with the administration method and administration form of the pharmaceutical composition. The pharmaceutical carriers may be such physiologically compatible buffers as Hank's or Ringer's solution, physiological saline, a mixture consisting of saline and glucose, and heparinized sodium-citrate-citric acid-dextrose solution. The pharmaceutical composition is orally or parenterally administered in accordance with the object of treatment, and can be prepared as a preparation such as powder, granules, a solution for injection or oral administration, tablets, suppositories, pessaries, ointment, cream or aerosol, using appropriate pharmaceutical carriers in accordance with the administration method.

When the pharmaceutical composition is directly administered as an injection to a patient, the polypeptide or its salt of the invention can continuously or intermittently administered in an amount of 10 to 5,000 mg per kg of human body weight and per one day and by intravenous drip as a solution in physiological saline.

6. EXAMPLES

The present invention is further embodied in the examples shown below which are not intended to limit the invention.

In the examples herein, the synthesis of polypeptide (1) is described. Additionally, the results of anti-HIV activity assays for the polypeptides of the invention and known high endotoxin affinity polypeptides are disclosed. Polypeptides of the invention have a significantly higher anti-HIV activity than known high endotoxin affinity polypeptides.

Apparatuses and reagents used in the following examples are as follows:

HPLC apparatus: Shimadzu Corporation, Model LC-6AD

Column of the apparatus: Asahipak ODP-90 (Asahi Chemical Industry Co., Ltd.)

Fmoc amino acid and amino resin: produced by Watanabe Chemical Industries, Ltd.

Condensing agent: produced by Peptide Institute, INC. and Applied Biosystems Japan FAB-MS (FAB-mass spectrograph): VC Co. (USA), Model ZAB-SE

6.1. EXAMPLE 1

SYNTHESIS OF THE POLYPEPTIDE (1)

The synthesis of a polypeptide (1) which has the formula shown below is described in Sections 6.1.1–6.1.7, infra. Polypeptides (2-13,22,23) and precursor peptides of polypeptides(14-21,24, 25)(see Table I, supra for structures) are synthesized using similar procedures.

```
  1     2    3    4    5    6     7     8    9    10   11   12   13   (1)
 Arg — Arg — Trp — Cys — Tyr — Arg — Lys — DLys — Pro — Tyr — Arg — Lys — Cys — Arg — NH₂
                   |________________________________________________|
```

In the above formula (1), Arg, Trp, Cys, Tyr, Lys, DLys and Pro denote the aforementioned amino acid residue, and the solid line between the Cys at the 3- and 11- positions denotes disulfide linkage.

6.1.1. INTRODUCTION INTO AN AMINOMETHYL RESIN OF Fmoc-DMBHA-CH₂CH₂COOH

[(3-(α-Fmoc-amino-4-methoxybenzyl)-4-methoxyphenyl)propionic acid]

270 mg (0.2 mmole) of an aminomethyl resin (0.74 meq/g) and 268.5 mg (0.5 mmole, 2.5 eq) of Fmoc-DMBHA-CH₂CH₂COOH (MW 537) were placed in a solid phase synthesizing column, and the condensation reaction was carried out for 2 hours by the method of DIPCDI-HOBt in DMF according to the method of Guo, L. et al. [Chem. Pharm. Bull., 36, 4989 (1988)].

After the completion of the condensation reaction, coupling was carried out for the protection of the free amino groups using acetic anhydride (DMBHA resin).

6.1.2. INTRODUCTION OF ARGININE AT THE 12-POSITION INTO THE DMBHA RESIN

After removing the Fmoc groups from the DMBHA resin prepared in Section 6.1.1., supra, with 20% piperidine/DMF, 2.5 equivalents (eq) of Fmoc-Arg(Pmc)-OH based on the DMBHA resin was added, and the condensation reaction was carried out in DMF according to the DIPCDI-HOBt method.

The degree of progress of the condensation reaction was pursued by measurement according to the ninhydrin test of Kaiser, E. et. al. [Anal. Biochem., 34, 595 (1970)].

6.1.3. INTRODUCTION OF CYSTEINE AT THE 11-POSITION

After the removal of the Fmoc groups from the DMBHA resin prepared in 6.1.2 with 20% piperidine/DMF, 2.5 eq of Fmoc-Cys (Trt)-OH based on the DMBHA resin was added, and condensation reaction was carried out in DMF by the method of DIPCDI-HOBt. The degree of progress of the condensation reaction was pursued similarly to 6.1.2., supra by measurement according to the ninhydrin test.

6.1.4. INTRODUCTION OF AMINO ACIDS FROM THE 10-TO 1-POSITIONS

Likewise as above, Lys(Boc), Arg(Pmc), Tyr(tBu), Pro, DLys(Boc), Lys(Boc), Arg(Pmc), Tyr(tBu), Cys(Trt), Trp, Arg(Pmc) and Arg(Pmc) were successively introduced into the DMBHA resin to obtain a protecting group-protected peptide (1) resin.

Each amino acid condensation reaction in the solid phase synthesis was carried out according to the operation conditions of the Table 2.

TABLE 2

| Operation | Reagent | Solvent | Time × Repeat number |
|---|---|---|---|
| Removal of Fmoc Group | 20% piperidine/DMF | DMF | 5 min. × 3 |
| Washing | — | DMF | 1 min. × 6 |
| Condensation reaction | Fmoc amino acid (2.5 eq) + DIPCDI + HOBt | DMF | 2 hr. × 1 |
| Washing | — | DMF | 1 min. × 4 |

6.1.5. PREPARATION OF THE POLYPEPTIDE (1) BY THE REMOVAL OF THE PROTECTING GROUPS. REMOVAL OF POLYPEPTIDE (1) FROM THE RESIN AND PARTIAL PURIFICATION

The protecting group-protected polypeptide (1) resin was subjected to 20% piperidine/DMF treatment to remove the Fmoc group, and then subjected to reaction at 25° C. for 2 hours in a 1M TMSOTf-thioanisole/TFA(trifluoroacetic acid) system (10 ml of trifluoroacetic acid in the presence of m-cresol (100 eq) and ethanedithiol (300 eq)) per 100 mg of the resin. The resin was filtered off from the reaction mixture and washed twice with 1 ml of trifluoroacetic acid. 100 ml of ice-cooled dry ether was subsequently added to mixture of the filtrate and the washing. The formed precipitate was centrifuged, and the residue was separated from the supernatant by decantation. The resulting residue was washed with cold ether, dissolved in 10 ml of 4N AcOH and 830 mg, 80 eq of dithiothreitol was added. The mixture was stirred at room temperature overnight.

The reaction solution was centrifuged, the supernatant was treated with Sephadex G-10 (3.7×5 cm), gel filtered with 4N acetic acid (AcOH), and the fraction which flowed through the Sephadex was collected as the main eluate part and lyophilized to obtain as powder, a partially purified noncyclized polypeptide (1).

6.1.6. PREPARATION OF THE POLYPEPTIDE (1) BY AIR OXIDATION

A half amount of the flow-through fraction by the Sephadex gel filtration was adjusted to pH 7.5 with concentrated aqueous ammonia, and subjected to air oxidation by aeration to carry out the cyclization reaction. After the completion of air oxidation, the cyclized polypeptide (1) was adsorbed onto 10 g of Diaion HP-20 resin, and subsequently eluted with 60% $CH_3CN$ (in 1N AcOH).

The eluate was concentrated at room temperature under reduced pressure to remove $CH_3CN$ and then lyophilized to give powder. The powder was dissolved in a small amount of water, and the solution was poured on an Asahipak ODP-90 column and purified by high performance liquid chromatography (HPLC-Model LC-6AD produced by Shimadzu Corp.) using gradient elution with $CH_3CN$ to obtain the polypeptide (1) of a single peak in a yield of 27% (a value calculated based on the protecting group-protected polypeptide (1) resin).

6.1.7. ANALYSIS OF THE POLYPEPTIDE

The amino acid composition after acid hydrolysis according to the method of Liu et al. [J. Biol. Chem., 251, 1936 (1976)] and that obtained by leucine aminopeptidase digestion of the polypeptide purified as in Section 6.1.6., supra, were found to be well accorded within the calculated value of the composition based on the amino acid sequence of the formula (1).

Further, the molecular weight value obtained by FAB-MS was 1996.3, while the calculated value of $[M+H]^+$ is 1996.1.

The specific rotation $[\alpha]^{20}_D$ of the obtained polypeptide was -17.2°(C=0.11, 1N acetic acid).

6.2 EXAMPLE 3

SYNTHESIS OF A POLYPEPTIDE (14)

[N-α-ACETYLATION OF THE AMINO TERMINAL AMINO ACID RESIDUE OF THE POLYPEPTIDE (1)]

The synthesis of a polypeptide (14) of the following formula 9 is described in Sections 6.2.1–6.2.2:

[Formula 9]

In the above formula (14), Ac-Arg, Arg, Trp, Cys, Tyr, Lys, DLys and Pro denote the aforementioned amino acid residues, and the solid line between the Cys at 3- and 11-positions denote a disulfide bond.

6.2.1 ACETYLATION OF THE PARTIALLY PROTECTING GROUP-PROTECTED PEPTIDE (1) RESIN 1.301 g (0.25 mmol) of the protecting group-protected peptide (1) resin obtained at the step (4) (Section 6.1.4) of the aforementioned EXAMPLE 1 was taken in a reaction vessel of a manual solid phase synthesis. After removal of the Fmoc group, the N-terminal amino group was acetylated according to the Hudson method [J. Org. Chem., 53, 617, (1988)] to obtain 1.241 g of an N-terminal α-amino acid-acetylated protecting group-protected peptide (1) resin (yield of dry weight, 100%). The procedure is summarized in the following Table 3.

TABLE 3

| # Operation | | Reagent | Solvent (volume) | Time × Repeat number |
|---|---|---|---|---|
| 1 Washing | | | DMF (15 ml) Isopropanol (15 ml) Dichloromethane (15 ml) DMF (15 ml) | each 2 min. × 3 |
| 2 Acylation | (i) | AcOH, 0.057 ml (1.0 mmol) + reaction | DMF (6 ml) | 3 min. × 1 HOBt, 153 mg (1.0 mmol) |
| | (ii) | BOP reagent*¹ 442.3 mg (1.0 mmol) | DMF (2 ml) | 3 min. × 1 |
| | (iii) | Diisopropylethylamine 0.35 ml (2 mmol) | DMF (2 ml) | 60 min. × 1 |
| 3 Washing | | | DMF (15 ml) Isopropanol (15 ml) Dichloromethane (15 ml) DMF (15 ml) | each 2 min. × 3 |

*¹BOP reagent: Benzotriazole-1-yl-oxy-tris-(dimethylamino)-phosphoniumhexafluorophosphate The acetylation was carried out by repeating the above operations 1 to 3, until the ninhydrin reaction became no more positive.

6.2.2 PREPARATION OF THE PEPTIDE (14) BY THE REMOVAL OF THE PROTECTING GROUPS AND THE RESIN OF THE N-TERMINAL AMINO ACID-ACETYLATED PROTECTING GROUP-PROTECTED PEPTIDE (1) RESIN, PARTIAL PURIFICATION AND OXIDATION

The polypeptide (14) was prepared by the same way as described in 6.1.5 and 6.1.6 supra. The specific rotation $[\alpha]^{20}_D$ of the polypeptide (14) was −18.3° (c=0.08, 1N acetic acid). The polypeptide (14) was acid-hydrolyzed in 4M methanesulfonic acid containing 0.2% tryptamine at 115° C. for 24 hours according to the method of Liu et al. [J. Biol. Chem., 251, 1936 (1976)]. The result of the amino acid analysis accorded well with the calculated value.

6.3 EXAMPLE 4

SYNTHESIS OF A POLYPEPTIDE (19)

[N-α-FLUORESCEINTHIOCARBAMOYL POLYPEPTIDE (1)]

The synthesis of a polypeptide (19) of the following formula 10 was carried out by N-α-fluoresceinthiocarbamoylation of the amino terminal amino acid residue of the polypeptide (1).

[Formula 10]

(19)

In the above formula (19), FTC-Arg, Arg, Trp, Cys, Tyr, Lys, DLys and Pro denote the aforementioned amino acid residues, and the solid line between the Cys at 3- and 11-positions denote a disulfide bond.

10 mg (3.9 μmol) of the acetic acid salt of the polypeptide (1) obtained in 6.1.6 was dissolved in 1 ml of PBS buffer (phosphate buffered saline, pH 7.5). To the solution, 2.8 mg (7.2 μmol) of fluorescein isothiocyanate (FITC) isomer-I (Wako Pure Chemical Ind., Ltd.) dissolved in 1 ml of DMSO was added under ice-cooling. After 6 to 7 hours of stirring at room temperature, the free amino group was fluoresceinthiocarbamoylated.

The reaction mixture was applied to a Sephadex G-25 (fine) column [equilibrated with 50 mM PB (phosphate buffer), pH 4.2], preliminarily desalted and fractionated. The peptide fraction was adsorbed on a Sep-Pak C 18 plus ENV cartridge column (Millipore Co.), eluted with an 80% acetonitrile/aqueous acetic acid solution pH 4.2 and freeze-dried to obtain 3.93mg of an acetic acid salt of the polypeptide (19) (yield, 35%).

The specific rotation $[\alpha]^{20}_D$ of the acetic acid salt of the obtained polypeptide (19) was −5.9° (C=0.06, H₂O).

The amino acid analysis of the acid hydrolysates of this compound according to the Liu method showed one less observed value of arginine residues than the calculated value for the polypeptide (1).

By thin layer chromatography (n-butanol:acetic acid:water =4:1:1) of partial acid hydrolysates of this compound in trifluoroacetic acid (room temperature for 2 hours), one main spot was detected, which corresponds to that of FTH-Arg (fluorescein arginine thiohydantoin).

The results of these analyses indicate that the α-amino group of the N terminal arginine residue is selectively fluorescein thiocarbamoylated.

6.4 EXAMPLE 2 AND COMPARATIVE EXAMPLES 1 AND 2
ANTIVIRAL ACTIVITY AGAINST HUMAN IMMUNODEFICIENCY VIRUS (HIV)

The antiviral activity against HIV of the polypeptide (1) synthesized in Example 1 was tested and evaluated according to the following method.

HIV-infected MT-4 cells (2.5×10⁴ cells/well, multiplicity of infection (MOI): 0.001) immediately after infection were added together with the test substance with various changes of the concentration to a 96-well microtitre plate. After incubation at 37° C. for 5 days in a $CO_2$ incubator, the number of survivor cells was measured by the MTT method [Pauwels et al.; J. Virol. Methods, 20, 309–321 (1988)]. The antiviral activity is expressed as a concentration at which cell death due to HIV infection is 50% inhibited ($EC_{50}$: 50% effective concentration). On the other hand, in order to know the cytotoxicity of the test substance on the MT-4 cells, virus-non-infected cells were incubated, likewise as above, together with the test compound with various changes of the concentration. The cytotoxicity is expressed as 50% cytotoxic concentration ($CC_{50}$) due to the test substance. Further, the rough ratio of $CC_{50}$ to $EC_{50}$, ($CC_{50}/EC_{50}$) is expressed as an effective ratio (SI).

The following formula 8 represents the peptide antiviral agent used in comparison with the polypeptide (1): Formula 8

(Arg-Arg-Trp-Cys-Tyr-Arg-Lys-Cys-Tyr-Lys-Gly-Tyr-Cys-Tyr-Arg-Lys-Cys-Arg-$NH_2$ (T-22)

Table 4 shows the $EC_{50}$, $CC_{50}$, and SI values of polypeptide (1), the above peptide(T-22) and anti-HIV agent AZT.

TABLE 4

| Test compound | | $CC_{50}$ (μg/ml) | $EC_{50}$ (μg/ml) | SI |
|---|---|---|---|---|
| Example 2 | Polypeptide(1) | 49.8 | 0.0034 | 14,647 |
| Comparative Example 1 | T-22 | 54.1 | 0.0099 | 5,465 |
| Comparative Example 2 | AZT (azidothymidine) μM | 6.68 | 0.0001 | 66,800 |

The above table apparently shows that the polypeptide (1) of the invention has the same cytotoxicity as that of T-22, whose anti-HIV activity was previously revealed, but exhibits an antiviral activity at one-third the concentration of T-22. Even though 4 amino acid residues have been removed from the peptide and the molecular weight has been lowered, the polypeptide of the invention exhibited an even higher activity.

In comparison with the azidothymidine(AZT), the $EC_{50}$ value of the polypeptide (1) is slightly higher, but it exhibited extremely low cytotoxicity. Therefore we expect that it can be used as a safer anti-HIV agent.

6.5 EXAMPLE 5

THE CHARACTERISTICS OF THE POLYPEPTIDES AND THEIR ANTI-HIV ACTIVITY

Table 5 shows the structural formula and the characteristics of the polypeptides of the invention prepared by the procedure of Examples 1, 3 and 4. Table 5 also shows anti-HIV activity of the polypeptides tested and evaluated according to the method of Example 2.

TABLE 5

| | Physical Property |
|---|---|
| Compound (Mame) & Structure | $[\alpha]_D^{20-22}$ (Conc., Solvent) |
| (1) Arg—Arg—Trp—Cys—Tyr—Arg—Lys—DLys—Pro—Tyr—Arg—Lys—Cys—Arg—$NH_2$ | −17.2 (0.11, 1NAcOH) |
| (3) Arg—Arg—Trp—Cys—Tyr—Arg—Lys—Lys—Gly—Tyr—Arg—Lys—Cys—Arg—$NH_2$ | −0.9 (0.04, 1NAcOH) |
| (5) Arg—Arg—Trp—Cys—Tyr—Arg—Lys—Pro—DLys—Tyr—Arg—Lys—Cys—Arg—$NH_2$ | −12.1 (0.06, 1NAcOH) |
| (6) Arg—Arg—Trp—Cys—Tyr—Arg—Lys—DOrn—Pro—Tyr—Arg—Lys—Cys—Arg—$NH_2$ | −12.5 (0.10, 1NAcOH) |
| (14) Ac—Arg—Arg—Trp—Cys—Tyr—Arg—Lys—DLys—Pro—Tyr—Arg—Lys—Cys—Arg—$NH_2$ | −18.3 (0.08, 1NAcOH) |
| (17) Myr—Arg—Arg—Trp—Cys—Tyr—Arg—Lys—DLys—Pro—Tyr—Arg—Lys—Cys—Arg—$NH_2$ | −19.1 (0.08, 1NAcOH) |
| (19) FTC—Arg—Arg—Trp—Cys—Tyr—Arg—Lys—DLys—Pro—Tyr—Arg—Lys—Cys—Arg—$NH_2$ | −5.9 (0.06, $H_2O$) |
| (22) Arg—Arg—Trp—Cys—Tyr—Arg—Lys—DLys(ε-N—Ac)—Pro—Tyr—Arg—Lys—Cys—Arg—$NH_2$ | −13.6 (0.07, 1NAcOH) |
| (23) Arg—Arg—Trp—Cys—Tyr—Arg—Lys—DLys(ε-N—But)—Pro—Tyr—Arg—Lys—Cys—Arg—$NH_2$ | −12.7 (0.10, 1NAcOH) |

| | Anti-HIV Activity | | |
|---|---|---|---|
| Compound (Mame) & Structure | $CC_{50}$ (μg/ml) | $EC_{50}$ (μg/ml) | SI ($CC_{50}/EC_{50}$) |
| (1) Arg—Arg—Trp—Cys—Tyr—Arg—Lys—DLys—Pro—Tyr—Arg—Lys—Cys—Arg—$NH_2$ | 65.37 | 0.0195 | 3352 |
| (3) Arg—Arg—Trp—Cys—Tyr—Arg—Lys—Lys—Gly—Tyr—Arg—Lys—Cys—Arg—$NH_2$ | 198.18 | 0.057 | 3477 |
| (5) Arg—Arg—Trp—Cys—Tyr—Arg—Lys—Pro—DLys—Tyr—Arg—Lys—Cys—Arg—$NH_2$ | 101.20 | 0.076 | 1321 |
| (6) Arg—Arg—Trp—Cys—Tyr—Arg—Lys—DOrn—Pro—Tyr—Arg—Lys—Cys—Arg—$NH_2$ | 55.93 | 0.021 | 2728 |
| (14) Ac—Arg—Arg—Trp—Cys—Tyr—Arg—Lys—DLys—Pro—Tyr—Arg—Lys—Cys—Arg—$NH_2$ | 78.14 | 0.024 | 3256 |
| (17) Myr—Arg—Arg—Trp—Cys—Tyr—Arg—Lys—DLys—Pro—Tyr—Arg—Lys—Cys—Arg—$NH_2$ | 106.60 | 0.055 | 1838 |
| (19) FTC—Arg—Arg—Trp—Cys—Tyr—Arg—Lys—DLys—Pro—Tyr—Arg—Lys—Cys—Arg—$NH_2$ | 38.47 | 0.001 | 39285 |
| (22) Arg—Arg—Trp—Cys—Tyr—Arg—Lys—DLys(ε-N—Ac)—Pro—Tyr—Arg—Lys—Cys—Arg—$NH_2$ | 44.26 | 0.030 | 1475 |
| (23) Arg—Arg—Trp—Cys—Tyr—Arg—Lys—DLys(ε-N—But)—Pro—Tyr—Arg—Lys—Cys—Arg—$NH_2$ | 138.07 | 0.0165 | 11095 |

TABLE 5-continued

| Comparative Example: | | | |
|---|---|---|---|
| T-22 | 49.4 | 0.017 | 2889 |
| AZT | 8.53 | 0.0014 | 6093 |

Unless otherwise specifies, the Cys at the 3- and 11- positions of the example compounds presented in the above tables are linked by a disulfide bond. Further, in the above table, "AZT" denotes azidothymidine (commonly known as zidovudine), and T-22 denotes the polypeptide represented in formula 8.

[Effectiveness of the invention]

The present invention provides a novel polypeptide having antiviral activity against human immunodeficiency virus (HIV) and it has make possible to give hydrophylicity, affinity for lipids, more higher activity and useful for elucidating the manifestation mechanism of anti-HIV activity.

We claim:

1. A polypeptide represented by the following formula or salt thereof in which $A_1$ is a basic amino acid residue, or a peptide residue having at least two basic amino acids, selected from the group consisting of lysine, arginine and ornithine, said basic amino acid residue or peptide residue in which N-α hydrogen atom of amino terminal end of said amino acid residue may be replaced with an acyl group or a substituted thiocarbamoyl group, forming N-α acyl substituted basic amino acid residue, N-α acyl substituted peptide residue, N-α substituted thiocarbamoyl group substituted basic amino acid residue or N-α substituted thiocarbamoyl group substituted peptide residue;

$A_2$ is a tyrosine or phenylalanine residue;

$A_3$ is a lysine or arginine residue;

$A_4$ is an —OH (derived from a carboxyl group) or an —$NH_2$ (derived from an acid amide group);

X is a peptide residue selected from the group consisting of the peptides represented by D-ornithyl-proline, prolyl-D-ornithine, D-lysyl-proline, prolyl-D-lysine, D-arginyl-proline, prolyl-D-arginine, glycyl-ornithine, ornithyl-glycine, glycyl-lysine, lysyl-glycine, glycyl-arginine and arginyl-glycine, in which the hydrogen atom of the ω-amino group of D-lysine, L-lysine, D-ornithine and L-ornithine may be replaced by an ω-amino acyl group, and said peptide residue is connected to the amino acid residues at the 6th and the 8th positions via peptide bond per se;

Trp is a tryptophan residue; and

Cys is a cysteine residue.

2. The polypeptide or salt thereof of claim 1 in which $A_1$ is at least one basic amino acid selected from the group consisting of lysine, arginine and ornithine.

3. The polypeptide or salt thereof of claim 1 in which $A_1$ is peptide residue of two basic amino acids, in which said amino acids are selected from the group consisting of lysine, arginine and ornithine.

4. The polypeptide or salt thereof of claim 1 in which $A_1$ is at least one basic amino acid residue in which N-α hydrogen atom of the amino terminal end of the amino acid residue is replaced with an acyl group or a substituted thiocarbamoyl group.

5. A polypeptide represented by the following formula or salt thereof in which $A_1$ is a basic amino acid residue, or a peptide residue having at least two basic amino acids, selected from the group consisting of lysine, arginine and ornithine, said basic amino acid residue or peptide residue in which N-α hydrogen atom of amino terminal end of said amino acid residue may be replaced with an acyl group or a substituted thiocarbamoyl group, forming N-α acyl substituted basic amino acid residue, N-α acyl substituted peptide residue, N-α substituted thiocarbamoyl group substituted basic amino acid residue or N-α substituted thiocarbamoyl group substituted peptide residue;

$A_2$ is a tyrosine or phenylalanine residue;

$A_3$ is a lysine or arginine residue;

$A_4$ is an —OH (derived from a carboxyl group) or an —$NH_2$ (derived from an acid amide group);

X is a peptide residue selected from the group consisting of the peptides represented by D-ornithyl-proline, prolyl-D-ornithine, D-lysyl-proline, prolyl-D-lysine, D-arginyl-proline, prolyl-D-arginine, glycyl-ornithine, ornithyl-glycine, glycyl-lysine, lysyl-glycine, glycyl-arginine and arginyl-glycine, in which the hydrogen atom of the ω-amino group of D-lysine, L-lysine, D-ornithine and L-ornithine may be replaced by an ω-amino acyl group, and said peptide residue is connected to the amino acid residues at the 6th and the 8th positions via peptide bond per se;

Trp is a tryptophan residue; and

Cys is a cysteine residue; and the cysteine residues at the 3- and 11- positions are linked through a disulfide linkage.

6. A pharmaceutical composition for inhibiting HIV activity in a patient comprising an effective amount of the polypeptide or salt thereof of claim 1 and a pharmaceutical carrier.

7. A pharmaceutical composition for inhibiting HIV activity in a patient comprising an effective amount of the polypeptide or salt thereof of claim 5 and a pharmaceutical carrier.

\* \* \* \* \*